(12) United States Patent
Watzele et al.

(10) Patent No.: US 6,218,546 B1
(45) Date of Patent: *Apr. 17, 2001

(54) REAGENT FOR THE DETECTION AND ISOLATION OF CARBOHYDRATES OR GLYCAN RECEPTORS

(75) Inventors: Manfred Watzele; Erhard Fernholz; Herbert Von Der Eltz, all of Weilheim (DE)

(73) Assignee: Roche Diagnostics GmbH, Mannheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/733,736

(22) Filed: Oct. 18, 1996

(30) Foreign Application Priority Data

Oct. 19, 1995 (DE) .............................. 195 39 008

(51) Int. Cl.[7] ................ C07D 235/02; G01N 33/53; G01N 33/573
(52) U.S. Cl. ................ 548/304.1; 435/7.1; 435/7.4
(58) Field of Search .................. 435/7.5, 7.1; 548/364.1

(56) References Cited

U.S. PATENT DOCUMENTS

| | | | |
|---|---|---|---|
| 4,804,625 | 2/1989 | Morrison et al. | 435/7 |
| 5,252,743 | 10/1993 | Barrett et al. | 495/4 |
| 5,449,781 | 9/1995 | Varki et al. | 546/271 |

FOREIGN PATENT DOCUMENTS

| | | |
|---|---|---|
| 36 29 194 A1 | 3/1987 | (DE) . |
| 3629 194 A1 | 3/1987 | (EP) . |
| 61-107158 | 5/1986 | (JP) . |
| 5-194942A | 8/1993 | (JP) . |
| 06222059A | 8/1994 | (JP) . |

WO 87/04794  8/1987  (WO) .

OTHER PUBLICATIONS

International Publication No. WO87/04794 published Aug. 13, 1987.
Patent Abstracts of Japan, No. JP4236353.
Orr, The Journal of Biological Chemistry, Jan. 25, 1981, vol. 256, No. 2, The Use of the 2–Iminobiotin–Avidin Interation for the Selective Retrieval of Labeled Plasma Membrane Components.
Shinohara et al, Anal. Chem. 1996, 68, 2573–2579, Bifunctional Labeling Reagent for Oligosaccharides to Incorporate Both Chomophore and Biotin Groups.
Toomre, et al., "Advances In the Use Of Biotinylated Diaminopyridine (BAP) As A Versatile Fluorescent Tag For Oligosaccharides", Glycobiology, vol. 4, No. 5, pp. 653–663, 1994.
Ni, et al., "Surface–Enhanced Resonance Raman Study Of Avidin–Dye Interactions: A Model For Chromophore–Containing Proteins", Journal of Raman Spectroscopy, vol. 19, pp. 429–438, 1988.
Thomas, et al., "Resonance Raman Spectroscopic Studies of 2–(4'–Hydroxyphenylazo)– Benzoic Acid And Some Substituted Analogs–II. Binding To Avidin And Bovine Serum Albunin", Spectrochimica Acta., vol. 35A, pp. 1251–1255, 1979.
Leteux et al, Glycobiology, vol. 8.(3), pp. 227 to 236, 1998.*

* cited by examiner

Primary Examiner—Floyd D. Higel
(74) Attorney, Agent, or Firm—Arent Fox Kintner Plotkin Kahn

(57) ABSTRACT

The invention concerns compounds which have a chromophore and a group capable of binding to streptavidin or/and avidin and which are suitable for binding to molecules containing an aldehyde, ketone, hemiacetal or/and hemiketal group. In addition the invention concerns conjugates formed from these compounds as well as a method for the detection or isolation of carbohydrates or glycan receptors by means of such conjugates.

4 Claims, 9 Drawing Sheets

Fig. 1  Reaction scheme for the formation of a conjugate of biotinyl-L-3-(2-naphthyl)-alanine hydrazide and a saccharide in which the closed ring structure is retained.

REACTION SCHEME FOR SYNTHESIZING 2 - [2' - (4" - HYDROXY-
BENZENEAZO) BENZOIC ACID AMIDO] - ETHYL SEMICARBAZIDE

Chromatogram of the reaction of derivatized dextran hydrolysate with HABA semicarbazide (15 µg) on a Microsorb $NH_2$ column.

RP18 chromatogram of the reaction of 0.5 nmol biantennary decasaccharide (2) and biantennary undecasaccharide (1) in each case with HABA semicarbazide on an ODS Hypersil column.

RP18 chromatogram of the saccharide moiety of human transferrin cleaved by means of Endo F2 (1) and N-glycosidase F (2) after reaction with 2-[2'-(4''-hydroxybenzeneazo)-benzoic acid-amido]ethyl semicarbazide.

Fig.6

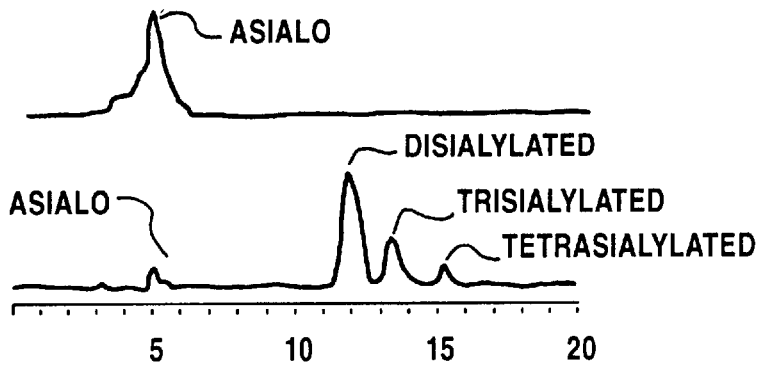

CHROMATOGRAM OF THE SUGAR OF FETUIN CLEAVED BY MEANS OF N-GLYCOSIDASE F AFTER DERIVATIZATION WITH HABA SEMICARBAZIDE ON AN ANION EXCHANGE COLUMN (TSK DEAE 5PW GLAS PAC; 75 x 8 mm) BEFORE AND AFTER DIGESTION OF THE SUGAR DERIVATIVES BY MEANS OF SIALIDASE.

Fig.11

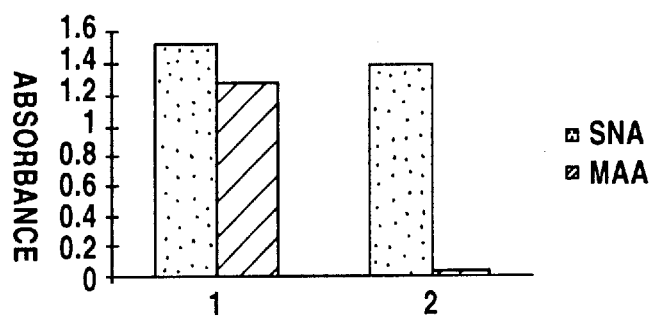

DETECTION OF FETUIN SUGAR DERIVATIVES (10 pmol) BEFORE (1) AND AFTER (2) DIGESTION OF THE SUGAR WITH NDV SIALIDASE USING THE DIGOXIGENIN-LABELLED LECTINS MAA AND SNA.

Fig. 7

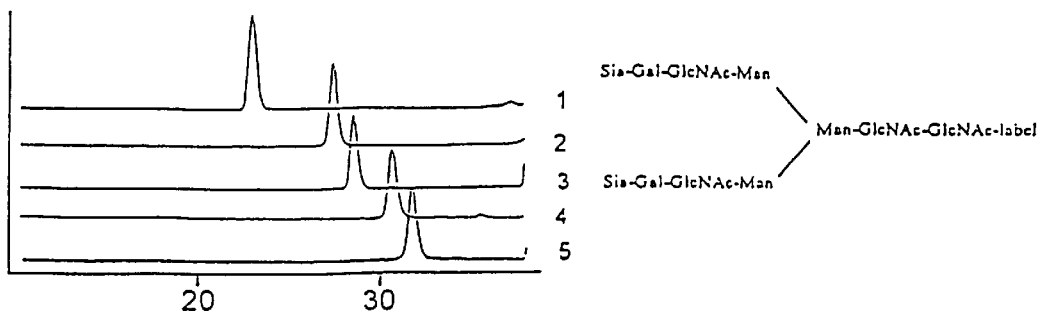

RP18 chromatograms of sugar residues cleaved by several
exoglycosidases from a biantennary undecasaccharide
after reaction with 2-[2'-(4''-hydroxybenzeneazo)-
benzoic acid amido]-ethyl semicarbazide:
1: without enzyme
2: with neuramidase
3: with neuramidase and ß-galactosidase
4: with neuramidase and ß-galactosidase and
   N-acetyl-ß-D-glucosaminidase
5: with neuramidase and ß-galactosidase and
   N-acetyl-ß-D-glucosaminidase and α-mannosidase.

Fig.8a

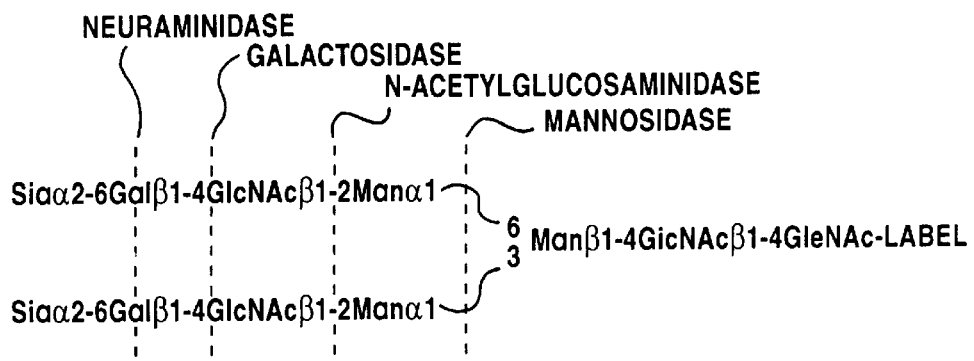

Fig.8b

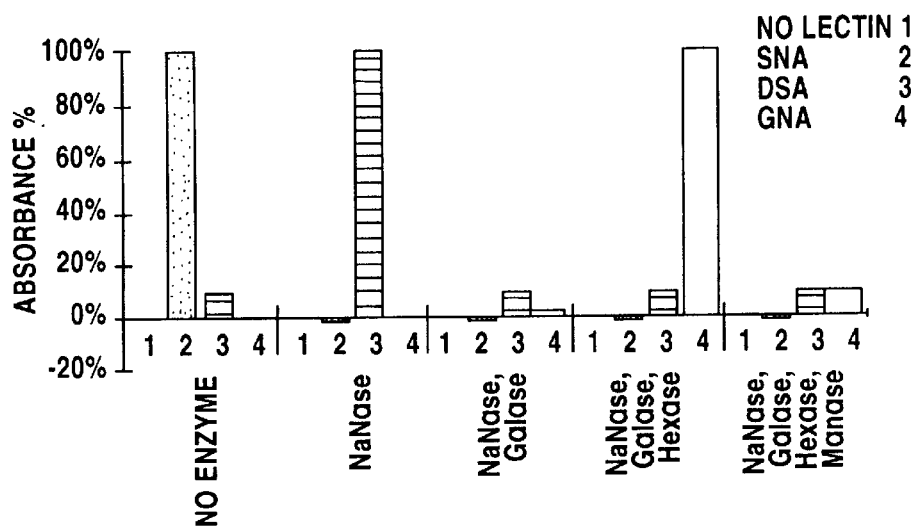

DETECTION OF BIANTENNARY UNDECASACCHARIDES CLEAVED SEQUENTIALLY WITH VARIOUS EXOGLYCOSIDASES (NaNase = NEURAMIDASE; GALASE = GALACTOSIDASE; HEXASE = N-ACETYLGLUCOSAMINIDASE; MANASE = MANNOSIDASE) AFTER FORMATION OF A CONJUGATE WITH 2-[2'-(4'''-HYDROXYBENZENEAZO) BENZOIC ACID-AMIDO]-ETHYL SEMICARBAZIDE AND DETECTION USING DIGOXIGENIN-LABELLED LECTINS (SNA, DSA AND GNA).

DETECTION OF INCREASING AMOUNTS OF FETUIN SUGAR DERIVATIVE (0-5 pmol) WITH DIGOXIGENIN-LABELLED LECTINS SNA AND MAA.

INFLUENCE OF INCREASING AMOUNTS OF N-ACETYLNEURAMINOSYL-2,3-D-LACTOSE DERIVATIVE (0-500 pmol) IN THE DETECTION OF FETUIN SUGAR DERIVATIVES (10 pmol) WITH DIGOXIGENIN-LABELLED MAA-LECTIN AND SNA-LECTIN.

Detection of various amounts in the range 0 to 5 pmol of conjugates of 3'sialyl Lewis X (columns 1 and 2) and 3' sulfatyl Lewis X (columns 3 and 4) by detection with an E-selectin fusion protein.

REAGENT FOR THE DETECTION AND ISOLATION OF CARBOHYDRATES OR GLYCAN RECEPTORS

DESCRIPTION

The invention concerns compounds which have a chromophore and a group capable of binding to streptavidin or/and avidin and are suitable for binding to molecules which contain an aldehyde, ketone, semiacetal or/and semiketal group. In addition the invention concerns conjugates formed from these compounds as well as a method for the detection or isolation of carbohydrates or glycan receptors by means of such conjugates.

Glycoconjugates are found in many biological areas for example as enzymes, transport proteins, receptor proteins, hormones or structural proteins. The interactions of free saccharides or saccharide moeities of the glycoconjugates with specific receptors play an important role in the biological function of these compounds.

In order to be able to investigate these interactions the appropriate saccharides have to be obtained in as pure a form as possible. Due to the great diversity of saccharides in natural samples and the structural similarity of many saccharides, it is, however, difficult to isolate pure defined saccharides. In particular the low UV sensitivity of saccharides hinders the detection of small amounts.

Various methods are known which are used to fractionate and detect saccharides. Analysis by means of high pH anion exchange (HPAE) chromatography with pulsed amperometric detection (PAD) allows the direct quantification of saccharides with a simple sample preparation without requiring a derivatization. However, the disadvantage of this method is that the strong basic conditions on the one hand have a detrimental effect on the saccharides and on the other hand they cannot be used directly in binding studies.

In a further method the saccharides are firstly derivatized. For this the saccharides are labelled with UV or fluorescence-active reagents such as e.g. by derivatizing with 2-aminopyridine (Rice et al., Anal. Biochem. 206 (1992), 278–287). The disadvantages of the method described in this reference are the high reaction temperatures which can lead to a decomposition of the saccharides (Kakehi et al., Anal. Biochem. 199 (1991), 256) and the use of toxic reagents such as e.g. NaCNBH$_3$. Moreover the conjugates obtained cannot be used directly in binding studies.

Methods for characterizing glycan-receptor interactions have also been described. In these methods soluble saccharides are derivatized in such a way that they can be bound to a solid phase or to macromolecules. This enables an examination of interactions between receptor and saccharide. For example in the method described by Feizi et al. (Feizi et al., Methods Enzymol. 230 (1994), 484–519) the saccharides are derivatized with a lipid and separated on thin layer plates. Subsequently the binding studies are carried out directly on the plate. However, a disadvantage of this method is the low sensitivity of the staining and detection of the saccharide. Moreover the separation is limited to a single separation technique namely thin layer chromatography. In addition the derivatization can be achieved by coupling oligosaccharides to neoglyco-proteins (Hubert et al., Cell. Diff. Dev. 27 (1989), 69) or directly to biotin. The derivatives obtained in this manner are, however, unsuitable for a conventional fractionation and detection so that firstly other methods have to be found for their purification.

Toomre and Varki prepared and used the reagent 2-amino6-amidobiotinyl-pyridine to attempt the detection and fractionation of saccharides and their direct characterization in binding studies with a single reagent (Toomre et al., Glycobiol. 4 (1994), 653–663). In this process a conjugate is formed from the saccharide and the reagent containing an amine group. Apart from the amine group the reagent also has the fluorescent properties of 2-aminopyridine and the affinity of biotin to streptavidin. As a result it was possible to carry out binding studies directly after a sensitive separation. However, disadvantages of this method are the different coupling efficiencies depending on the saccharide which are referred to in the patent application WO94/28008 by Varki and Hotenberg, the possible decomposition of the saccharides under the reaction conditions and the toxicity of the reducing agent.

Moreover as a result of the reductive amination step the sugar is always in an open-chain form at the reducing end and is no longer able to form a closed ring structure. Thus the formation of the conjugate modifies the structure of the saccharide. Since, however, it is the saccharide which represents the recognition structure which is to be examined, the specific receptor for the saccharide may possibly not bind to the saccharide which is a major disadvantage of this method.

Detection reagents that are suitable for examining the interactions of saccharides with receptors should ideally have the following properties:

the test reagent should contain a marker group by means of which the saccharides can be detected with high sensitivity by UV/VIS or fluorescence spectrometry, the conjugate which forms by coupling the saccharide to the detection reagent should be capable of binding to macromolecules or solid phases: this property can be used either to immobilize or to detect the saccharide, the saccharides should not be decomposed under the reaction conditions, it should be possible to have a closed ring structure at the reducing end of the sugar in the derivatization, it should be possible to separate derivatized saccharide mixtures in a simple manner, it should be possible in a relatively simple manner to separate the detection reagent which is usually used in excess for the derivatization from the reacted saccharides, the reagents required for the derivatization should have the lowest possible toxicity or be non-toxic, the efficiency of the coupling reaction should be high for all saccharides, the detection reagent should facilitate an analysis by means of mass spectrometry, the detection reagent should not influence the interaction between the saccharide and the ligand.

One object of the present invention was therefore to provide improved reagents for the detection and isolation of saccharides and glycan receptors.

This object is achieved according to the invention by a compound having a structure of the formula (I):

in which X represents a residue selected from —NR—NH$_2$, —C(A)—NR—NH$_2$ or —B—C(A)—NR—NH$_2$ in which R is hydrogen or an alkyl residue with 1 to 4 C atoms and A and B each independently represent NH, O or S and Y represents a residue which contains a chromophore as well as a ligand capable of binding to streptavidin or/and avidin.

Such a compound can be coupled via the residue X to ketone, aldehyde, semiketal or semiacetal groups which in particular are present in saccharides. The resulting conjugates have a chromophore group and are capable of binding to streptavidin or avidin. The compound (I) preferably has a high absorption value $\epsilon$ in the UV/VIS range and thus enables a sensitive detection of the substance to be detected. In addition the substance to be examined can be coupled to a solid phase or a macromolecule by the ligand capable of binding to avidin or/and streptavidin. As elucidated in more detail in the following the compound (I) can be coupled to saccharides under reaction conditions in which the saccharides are not decomposed. Furthermore no toxic reagents are required for the reaction. The compound (I) reacts selectively with the reducing end of saccharides while retaining their ability to form a closed ring structure. Moreover detection reagent added in excess can be simply separated by means of phase separation of the conjugates obtained.

X can represent a residue —NR—NH$_2$ which is bound to an alkylene, alkenylene or alkinylene group or to an aromatic group such as a hydrazine. In addition X can represent the group —B—C(A)—NR—NH$_2$ in which A, B and R are defined as above such as a semicarbazide, or a group —C(A)—NR—NH$_2$ such as a hydrazide.

It is preferred according to the invention that the chromophore which is contained in the residue Y has an absorption maximum at a wavelength $\lambda_{max}$ of more than 250 nm. This enables a sensitive detection in conventional UV/VIS spectrometers. If the chromophore also has fluorophore properties it is also possible to detect it with fluorescence detectors. In addition the chromophore preferably has a molar absorption coefficient $\epsilon$ of preferably more than 1000 l mol$^{-1}$cm$^{-1}$ and particularly preferably of more than 3000 l mol$^{-1}$cm$^{-1}$ at the wavelength $\lambda_{max}$ of the absorption maximum.

In a first preferred embodiment of the invention the ligand capable of binding to avidin or/and streptavidin is biotin or a biotin derivative in particular iminobiotin, diaminobiotin or desthiobiotin.

R in the compound (I) preferably denotes hydrogen. B in the case of semicarbazides preferably denotes NH and A in the case of hydrazides and semicarbazides preferably denotes O.

In a further preferred embodiment of the present invention the ligand capable of binding to avidin or/and streptavidin is itself a chromophore. In this case the compound X—Y can have a structure of formula (II):

(II)

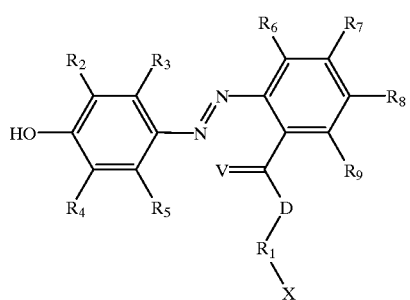

in which X is defined as above, V and D each independently represent NH, O or S, R$_1$ represents an alkylene, alkenylene or alkinylene group optionally containing heteroatoms with a length of 2 to 20 atoms and R$_2$ to R$_9$ each independently denote hydrogen or an alkyl group with 1 to 4 carbon atoms. The residues R$_2$ to R$_9$ preferably represent hydrogen. V is preferably oxygen. Furthermore it is preferred that B represents an NH group and R$_1$ denotes an alkylene group with 2 to 6 C atoms. in a particularly preferred embodiment of the compound of formula (II) the residue Y is a 2-[2'(4"-hydroxybenzeneazo)-benzoic acid-amido]ethyl residue. X—Y most preferably represents 2-[2'(4"-hydroxybenzeneazo)-benzoic acid-amido]ethyl semicarbazide.

Compounds having a structure of formula (II) can be prepared from compounds having a structure of formula (III)

(III)

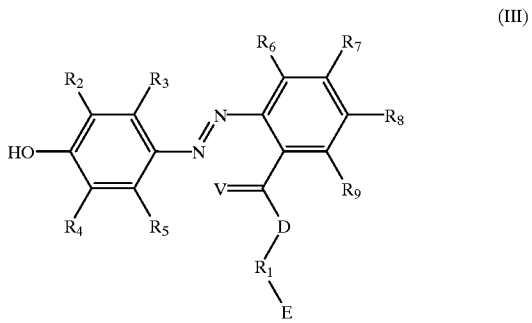

in which E represents a group selected from —OH, —SH, —NH$_2$ or —COOH. E preferably denotes —NH$_2$ or —COOH.

In a further preferred embodiment according to the invention the residue Y in the compound (I) contains a group Y$_1$ which comprises a chromophore and a group Y$_2$ which comprises a ligand capable of binding to streptavidin or/and avidin as well as a linear linking group L with a chain length of 1 to 10 atoms optionally containing heteroatoms wherein either Y$_1$ or Y$_2$ is bound as a side group to L. Such preferred compounds according to the invention have a structure of formula (IV):

(IV)

In such compounds the chromophore and the group capable of binding to streptavidin or/and avidin are linked together by means of a linker group.

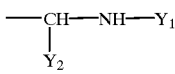

in which Y$_1$ represents a residue which contains a chromophore and Y$_2$ represents a residue which contains a ligand capable of binding to streptavidin or/and avidin. The chromophore and the bindable ligand are linked together in this embodiment via a CH—NH group.

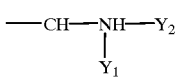

wherein Y$_1$ and Y$_2$ are defined as above.

In principle Y$_1$ can contain any desired chromophore. Y$_1$ preferably represents a group CHR—(CH$_2$)$_n$—Q in which n=0 to 20, R is hydrogen or an alkyl group and Q represents an aromatic or heteroaromatic residue preferably a naphthyl residue.

$Y_2$ can represent any desired residue which contains a ligand capable of binding to streptavidin or/and avidin. $Y_2$ is preferably selected from the groups —$((CH_2)_nV_q)$—K, —C(O)—$(CH_2)_nV)_q$—K and —$((CH_2)_m$—W—$(CH_2)_o)_p$—V—K in which V represents NH, O or S, K is biotin or a biotin derivative, W represents NH or O, n=0–20, m=0–6, p=0–4 and q=0 or 1. $Y_2$ is preferably a —$((CH2)_nV)_q$—K group in which n=1 to 7, q=0 or 1, V is NH and K is biotin.

In compounds of formula (IV) which contain a linker group between the chromophore and the group capable of binding to streptavidin or/and avidin X preferably represents the group —C(A)—NR—$NH_2$ in which A and R are defined as above. The compound X—Y is particularly preferably biotinyl-L-3-(2-naphthyl)alanine hydrazide. The biotinyl residue capable of binding to avidin or/and streptavidin can also be replaced by a biotin derivative in particular iminobiotin, diaminobiotin or desthiobiotin.

The invention also encompasses the use of the described compounds as a reagent to derivatize a substance containing an aldehyde, ketone, semiketal or semiacetal group e.g. of saccharides.

A further subject matter of the invention is a conjugate formed from a compound containing an aldehyde, ketone, semiketal or semiacetal group and a compound of formula (I). The compounds (I) react selectively with these functional groups and in this process form conjugates which have a capability of binding to avidin or/and streptavidin and contain a chromophore. Such a conjugate can have a structure of formula (V)

Z'—X'—Y                                         (V)

in which Z'—Y' is the reaction product of a compound containing an aldehyde, ketone, semiketal or semiacetal group with the group X and X and Y have the meanings stated before.

The compounds X—Y according to the invention are particularly suitable for forming a conjugate with a monosaccharide, disaccharide or oligosaccharide. It was surprisingly found that the compounds according to the invention react selectively with the reducing end of the sugar while preferably retaining its ability to form a closed ring structure. Thus saccharide derivatives of compounds of formula (II) can be present in an amount of more than 90% in the form of a closed ring structure.

A reaction scheme for forming a conjugate according to the invention is illustrated in FIG. 1. FIG. 2 shows a further reaction scheme in which the synthesis of a compound according to the invention is shown.

Conjugates of compounds (I) are particularly preferred in which the bindable ligand is itself a chromophore e.g. compounds (II). In addition conjugates of compounds (I) are particularly preferred in which Y has the structure (IV).

A further subject matter of the invention is a process for the production of a conjugate described above in which an aldehyde, ketone, semiketal or semiacetal is reacted with a compound (I) according to the invention under conditions in which the group X reacts with the aldehyde, ketone, semiketal or semiacetal group. A monosaccharide, disaccharide or oligosaccharide is used in particular as the aldehyde, ketone, semiketal or semiacetal.

Furthermore the invention encompasses complexes which are formed from such a conjugate and avidin or/and streptavidin. Such a complex preferably contains 1 to 4 mole equivalents of the conjugate per mole equivalent avidin or streptavidin. The avidin or streptavidin is particularly preferably present immobilized on a solid phase.

These complexes can be used as an immunogen to produce anti-glycan antibodies. For this the complexes are preferably admixed with an adjuvant e.g. complete Freund's adjuvant and administered several times at time intervals to an experimental animal e.g. a mouse. Antibodies against the sugar component of the complex can then be isolated from this experimental animal in a known manner. Reference is made to example 5 of WO 94/28008 for the exact experimental procedure.

The compounds, conjugates and complexes according to the invention enable carbohydrates to be selectively fractionated and sensitively detected which allows the detection and isolation of carbohydrates as well as the examination of interactions of carbohydrates with receptors. Therefore the invention in addition encompasses a method for the detection or isolation of carbohydrates comprising the steps:

(a) contacting a compound (I) according to the invention with a sample containing a carbohydrate to be detected or/and isolated, (b) forming a conjugate of the carbohydrate to be detected and the compound (I) and (c) detecting or/and isolating the conjugate.

For this the compounds (I) can on the one hand (i) be reacted to form the conjugates and (ii) subsequently be complexed with streptavidin or/and avidin by incubation. On the other hand the compounds (I) can also be (i) firstly complexed and (ii) subsequently be reacted to form the conjugates.

According to the invention it is preferable to use avidin or/and streptavidin bound to a solid phase such as e.g. a microtitre plate, a micro-reaction vessel, a membrane e.g. a nitrocellulose or PVDF membrane or optionally magnetic microbeads or a macromolecule in order to immobilize the conjugate. The detection and isolation of carbohydrates is preferably achieved by binding a glycan receptor. Glycan receptors are substances which specifically interact with carbohydrates of a defined structure. Examples of glycan receptors which can be used to detect or/and isolate specific carbohydrate structures are selecting, lectins and anti-glycan antibodies. Lectins and selectins bind very specifically to particular carbohydrate structures. The lectin MAA binds for example specifically to α(2-3) bound sialic acids which enables the detection of this group. Lectins are commercially available e.g. from Boehringer Mannheim, cf. Biochemical catalogue.

In order to detect carbohydrates it is preferable to use a glycan receptor which is directly or indirectly labelled. A label in this context is understood as the fact that the glycan receptor itself carries a marker group whereas indirect label means that a further reagent which is capable of binding to the glycan receptor carries the label.

The label can be any desired label, in particular the label can be radioactive or via a hapten, an enzyme, a metal complex, a luminescent or fluorescent marker. In addition the glycan receptor can be preferably determined according to the invention by means of an optionally labelled specific antibody. Lectins can for example be labelled with digoxigenin which enables a detection with labelled antidigoxigenin antibodies.

On the other hand conjugates of the compounds according to the invention with saccharides also enable a specific detection of glycan receptors i.e. glycan binding proteins, lectins etc. Therefore a further subject matter of the present invention is a method for the detection or/and isolation of glycan receptors comprising the steps:

(a) forming conjugates from one or several selected and thus known carbohydrates and a compound (I) according to the invention (b) contacting the conjugate with a sample containing a glycan receptor to be detected or/and isolated and (c) detecting or/and isolating the glycan receptor.

For this the conjugates can on the one hand (i) be converted into a complex by incubation with streptavidin or/and avidin and (ii) subsequently be contacted with the sample. On the other hand the conjugates can also be (i) contacted with the sample and (ii) subsequently be converted into a complex by incubation with streptavidin or/and avidin. The streptavidin or/and avidin is preferably bound to a solid phase so that the glycan receptor can be separated from the sample by means of its binding to the solid phase and detected in an isolated form. Specific examples of glycan receptors to be detected are mentioned in a review article by Varki (Glycobiol. 3 (1993), 97–130) such as lectins, selectins or cellular carbohydrate-containing surface structures e.g. E-selectin, P-selectin, L-selectin, CD44, CD22β or the macrophage Gal/Nac receptor. The method can also be used to identify and isolate unknown glycan receptors.

Conjugates and complexes according to the invention can be used in a labelled form to detect glycan receptors.

The glycan receptor to be detected or/and to be isolated can also optionally be labelled for example by an in vivo labelling with radioactive isotopes such as $^{35}S$ or $^{14}C$. On the other hand the label can also be introduced before or after binding of the receptor to the conjugate by chemical coupling e.g. with active esters or SH reagents.

The glycan receptor is preferably detected or isolated via its binding to a solid phase by which means it can be separated from the other components of the sample. After this separation the glycan receptor can be detached again from the solid phase if desired e.g. by displacement or adding a denaturing reagent. The detached glycan receptor which is optionally present in a labelled form can subsequently be further characterized by suitable methods e.g. by gel electrophoresis such as SDS-PAGE or by an immunological test such as an ELISA.

Furthermore the invention encompasses a reagent kit for the detection or/and isolation of carbohydrates comprising
(a) a compound (I) and
(b) a solid phase coated with streptavidin or/and avidin.

Solid phases which can for example be used are a microtitre plate, a micro-reaction vessel, a membrane or optionally magnetic microbeads. In addition the reagent kit can contain further reagents which can be used to determine carbohydrates. These include for example glycan receptors such as digoxigenin-labelled lectins and carbohydrate-cleaving enzymes.

Yet a further subject matter of the present invention is a reagent kit for the detection or/and isolation of glycan receptors comprising:
(a) a compound according to the invention which can optionally be present in the form of a conjugate with a specific saccharide for the glycan receptor that is to be detected or/and isolated and
(b) a solid phase coated with streptavidin or/and avidin.

The invention is elucidated in more detail by the following examples and attached figures in which FIG. 1 represents a reaction scheme for forming a conjugate from biotinyl-L-3—(2-naphthyl)-alanine hydrazide with a saccharide;

FIG. 6 shows the chromatogram of the saccharide moiety of fetuin cleaved by N-glycosidase F after derivatization with HABA-semicarbazide before (below) and after (above) digestion of the sugar derivatives with neuraminidase on an anion exchange column (example 3b);

FIG. 7 shows the RP18 chromatograms of a sequential cleavage of the sugar residues of a biantennary undecasaccharide by several exoglycosidases (example 4);

FIG. 8a shows the cleavage sites of the enzymes neuraminidase, galactosidase, N-acetylglucosaminidase and mannosidase on a biantennary undesaccharide (example 4);

FIG. 8b shows the detection using digoxigenin-labelled lectins (SNA, DSA and GNA) of saccharide derivatives from fragments of the saccharide shown in FIG. 8a which were produced by digestion with various enzymes (example 4);

Figure 12:
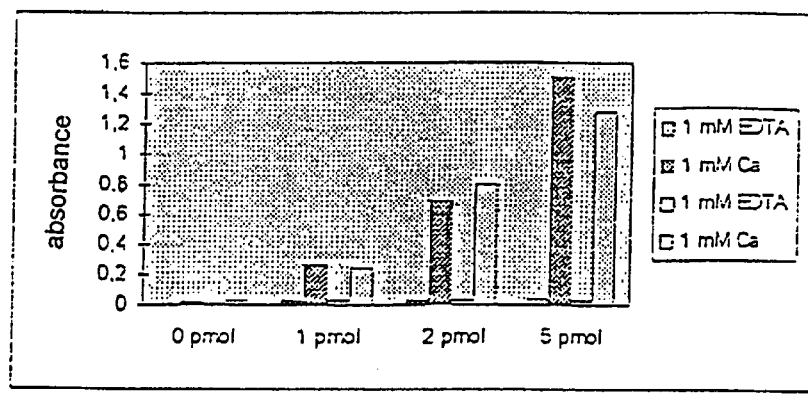

FIG. 11 shows the detection of fetuin sugar derivatives (10 pmol) before (1) and after (2) digestion with NDV sialidase using the digoxigenin-labelled lectins MAA and SNA (example 4) and FIG. 12 shows the detection of various amounts of 3'-sialyl Lewis X (columns 1 and 2) and 3' sulfatyl Lewis X (columns 3 and 4) with an E-selectin fusion protein (example 4).

The invention is elucidated in more detail by the following examples:

EXAMPLE 1

Preparation of 2-[2'-(4"-hydroxybenzeneazo)-benzoic acid amido]-ethylsemicarbazide 4

Figure 1:
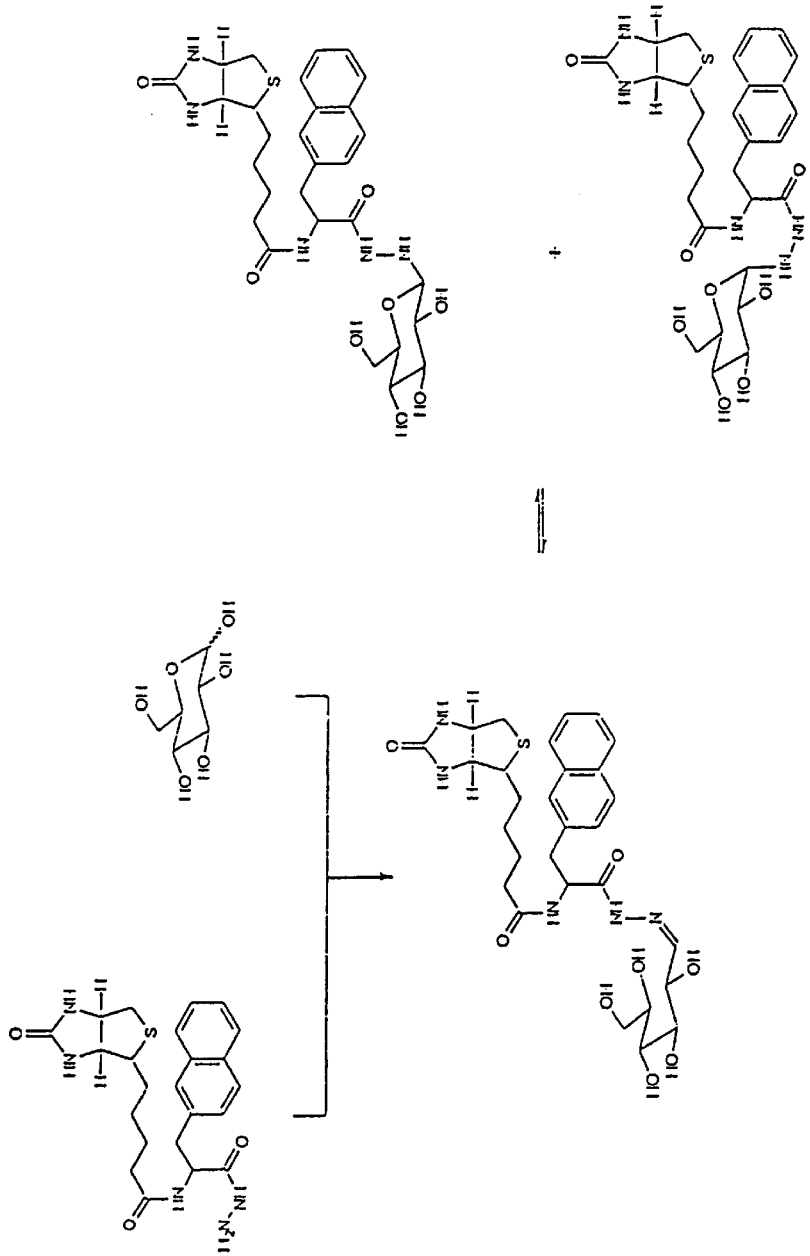
Figure 2:
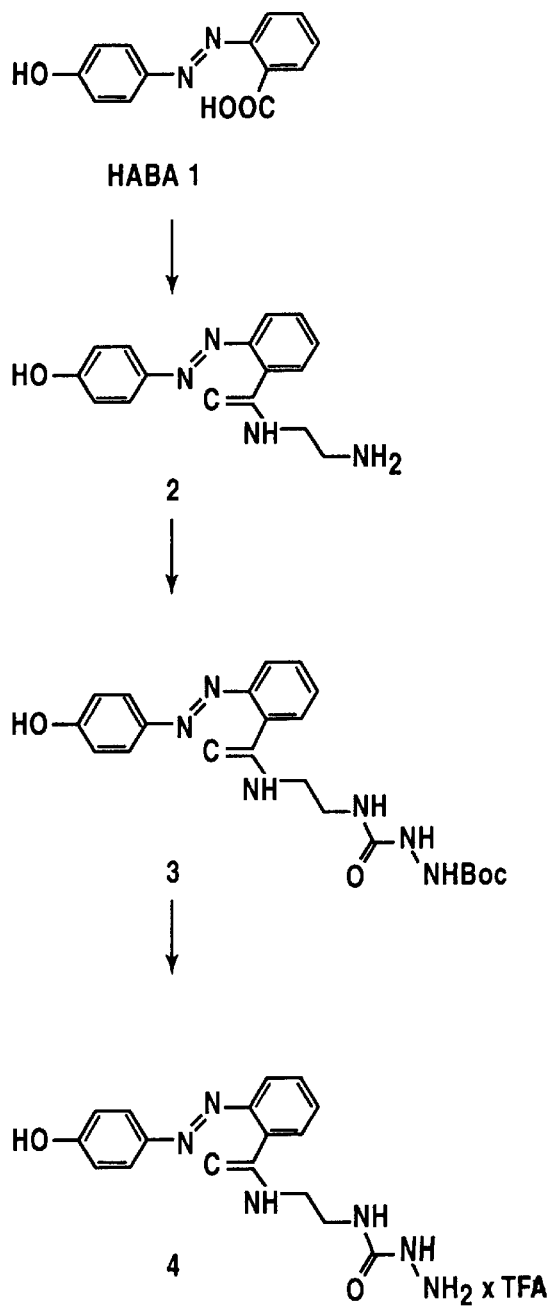
FIG. 2 shows a reaction scheme for the synthesis of the compound 2-[2'-(4"-hydroxybenzeneazo)-benzoic acid-amido]-ethylsemicarbazide (example 1)

The synthesis of 2-[2'-(4"-hydroxybenzeneazo)-benzoic acid amido]-ethylsemicarbazide proceeds according to the reaction scheme shown in FIG. 2.

Preparation of 2-[2'-(4"-hydroxybenzeneazo)-benzoic acid amido]-ethylamine 2

A solution of 10.3 g (50 mmol) N,N'-dicyclohexyl carbodiimide (DCC) (Fluka) in 50 ml THF is added dropwise to a solution of 6 g (25 mmol) 2-(4'-hydroxybenzeneazo)-benzoic acid 1 (HABA) (Aldrich) and 3 g (25 mmol) NHS (97% Fluka) in 50 ml dry tetrahydrofuran (THF) and stirred for a further 24 hours at room temperature.

Subsequently the precipitate that forms is removed by suction filtration, the filtrate is evaporated to dryness and the crude product obtained is filtered over silica gel (AcOEt:MeOH=6:1).

After removing the solvent the residue obtained is dissolved in 50 ml THF/MeOH (1:1) and added dropwise at room temperature to a solution of 5 ml ethylenediamine (75 mmol) (99%, Aldrich). The reaction solution is stirred for a further 0.5 h, then evaporated to dryness and the product is purified by chromatography (silica gel, MeOH). 1.5 g (20% over 2 steps) of compound 2 is obtained as an orange solid.

Preparation of 3.

0.66 g (5 mmol) t-butylcarbazole (99%, Aldrich) and a solution of 1.5 g (5 mmol) 2 in 20 ml anyhdrous DMF are added successively while stirring to a solution of 0.8 g (5 mmol) CDI (Aldrich) in 10 ml anhydrous DMF. It is stirred for a further 1 h at room temperature, the reaction mixture is then poured into 200 ml water and extracted with 2×200 ml ethyl acetate. The combined organic phases are washed successively with 200 ml 1 N HCl, 200 ml water, 200 ml 0.1 M phosphate buffer, pH 7.0 and 200 ml water and dried ($MgSO_4$). Finally it is filtered and the filtrate is freed of solvent. The crude product is firstly filtered (Sepharose LH 20, MeOH) and subsequently purified by column chromatography (silica gel, toluene:acetone:MeOH=1:1:0.1). 950 mg (40%) 3 is obtained as an orange solid.

$^1$H-NMR (100 MHz, $CD_3OD$): δ =1.44 (s, 9 H, Boc-protons); 3.30–3.61 (m, 4 H, N—$CH_2$—$CH_2$—N); 6.95 and 7.83 (4 H, AA'BB' system, H-C(2"), H-C(3"), H-C(5") and H-C(6")); 7.48–7.91 (m, 4 H, protons on C(3') to C(6')).

Preparation of 4.

2 ml TFA is added to a solution of 218 mg (0.5 mmol) 3 in 2 ml $CH_2Cl_2$ and stirred for 30 min. at 40° C. Subsequently the solvent is withdrawn in a vacuum, the residue is dissolved in a small amount of MeOH, 10 ml water is added and it is lyophilized. 205 mg (93%) 4 is obtained as an orange solid. The product can be used directly to label aldehydes and ketones.

MS [M+H] 343.1; $^1$H NMR (500 MHz, D6-DMSO): δ =3.26 (ψq, 2 H, $H_2$—C(1)); 3.37 (ψq, 2 H, $H_2$—C(2)); 6.96 and 7.77 (AA'BB' system, 4 H, H-C(2"), H-C(3"), H-C(5") and H-C(6")); 7.23 (t, 1 H, C(1)—NH—C(O)—N); 7.51–7.59 and 7.64–7.70 (2 m, 4 H, protons on C(3') to C(6')); 8.48 (t, 1 H, Ar—C(O)—HN—C(2')); 8.83 (br s, 1 H, C(O)—NH—N); 9.75 (br s, 2 H, N—$NH_2$); 10.5 (s, 1 H; phenolic OH)).

EXAMPLE 2

Derivatization of saccharides with 2-'[2'-(4"hydroxybenzeneazo)-benzoic acid-amido]-ethyl semicarbazide.

Reaction of Glucose:

A solution of 20.5 mg (0.06 mmol) of the marker in 5 ml MeOH:AcOH (10:1; v:v) is added to a solution of 11.4 mg (0.06 mmol) glucose (Merck) in 1 ml $H_2O$ and it is stirred for 18 h at 60° C. Subsequently the solvent is removed in a vacuum, the residue is dissolved in a small amount of MeOH, 10 ml water is added and the preparation is subsequently lyophilized. The crude product is purified by column chromatography (Sepharose LH 20, MeOH and RP18, 0.1% TFA in 17% $CH_3CN$). 17 mg (56%) of the glucose conjugate is obtained as an orange solid.

$UV_{max}$: 360 nm ($\epsilon_{360}$=17000 l $mol^{-1}cm^{-1}$). MS [M+H]: 505.2

$^{13}$C NMR (500 MHz, $D_6$-DMSO+$D_2$O): δ =91.2 (C-1), 70.5 (C-2), 77.2 (C-3), 71.4 (C-4), 77.8 (C-5), 62.0 (C-6); 39.2 ($H_2$—C(1)); 39.9 ($H_2$-C(2)); 115–150 (C atoms of the aromatic); 160.3 (Ar—C(O)-HN—C(2')); 168.1 (NH—C(O)—NH).

$^1$H NMR (500 MHz, $D_6$-DMSO+$D_2$O): δ =3.7 (1 H; H—C(1)), 3.0 (1 H; H-C(2)), 3.2 (1 H; H-C(3)), 3.0 (1 H; H-C(4)), 3.1 (1 H; H-C(5)), 3.7 (2 H; $H_2$—C(6)); 3.3 (2 H, $H_2$—C(1')); 3.5 (2 H, $H_2$—C(2')); 6.6 and 7.6 (AA'BB'system, 4 H, H-C(2"), H-C(3"), H-C(5") and H-C(6")); 7.5–7.6 and 7.3 (4 H, protons on C(3') to C(6')).

From the NMR data it can be deduced that the glucose derivative has a closed ring structure (B conformation). It is also possible to confirm this by structure calculation.

Reaction of Monosaccharides and Oligosaccharides:

a) Conversion rates:

In order to compare the conversion rates of various saccharides for analytical purposes 1 nmol glucose, N-acetyl-neuraminosyl-2,3-D-lactose (Boehringer Mannheim) biantennary undecasaccharide (BioCarb) and a triantennary sialylated oligosaccharide (Oxford Glyco Systems) are reacted for 12 h at 60° C. in 100 μl reaction mixtures in closable Eppendorf cups with a five-fold molar excess of marker 4 in MeOH. The reaction rate is determined by means of RP18 chromatography (ODS Hypersil 250×4.6 mm from the Bischoff Company; eluant A: 0.1% TFA in $H_2O$; eluant B: 0.1% TFA in $CH_3CH$; gradient 0–40% in 30 min) and determined by means of TLC (mobile solvent: MeOH:$H_2O$: butane-2-one=6:2:2; v:v:v; detection of sugar by means of 20% $H_2SO_4$ in EtOH).

After the derivatization free sugar could no longer be detected on the TLC which indicates a conversion rate >95%. In the HPLC analysis the areas of the conversion signals were comparable for all saccharides which indicates the same conversion rate for the various saccharides.

The limit of detection of the saccharide derivatives by means of UV detection is ca. 100 pmol. The marker elutes at ca. 30% $CH_3CN$ from the RP18 column and can thus be easily separated from the conjugates which elute at 10–20% $CH_3CN$.

b) Stabilities:

The saccharide conjugates show no manifestations of decomposition (according to HPLC analysis <5%) in solution at 25° C. (40 h) or after lyophilization. The marker 4 itself still shows no decomposition after one week in MeOH at 25° C.

c) Separation of the Marker Surplus:

The separation of the surplus marker after reaction with the saccharides is carried out by extraction with ethyl acetate. For this 100 μl redistilled $H_2O$ and 800 μl ethyl acetate are added to 100 μl reaction mixtures; after mixing and centrifugation (1 min at 10000 g) the upper ethyl acetate phase is removed and the extraction is repeated a further 2 times with the lower aqueous phase. In this process 90% of the marker can be separated. The loss of sugar conjugates tested using a glucose conjugate is below the detection limit of 5%.

EXAMPLE 3

Separation of Derivatized Saccharides on HPLC Columns

Figure 3:
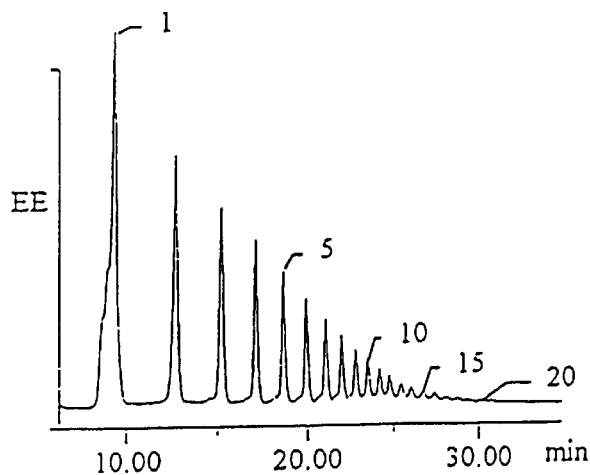
FIG. 3 shows a chromatogram of a reaction of derivatized dextran hydrolysate with HABA semicarbazide (15 μg) on a microsorb-NH2 column (example 3)

Analysis of a Dextran Hydrolysate:

A dextran hydrolysate (Oxford Glyco Systems) is conjugated with a marker and analysed. Using a carbohydrate CHO C18 column (220×2.1 mm; Perkin Elmer) and a linear gradient of 25–75% within 50 min (eluant A: 0.1 M $NH_4OAc$ pH 5.5 containing 10% $CH_3CN$; eluant B: 0.1 M $NH_4OAc$ pH 5.5 containing 25% $CH_3CN$; flow rate 0.2 ml/min) a separation of the glucose monomer up to the 17 mer oligosaccharide is obtained with an application quantity of 5 μg of the dextran hydrolysate conjugate. When the same dextran hydrolysate conjugated with marker 4 is analysed with a Microsorb-NH2 column (250×4.5 mm; Rainin) under the elution conditions stated below a separation up to the 20 mer oligosaccharide can be obtained with a 15 μg application quantity (FIG. 3.)

Eluant A: 10 mM $NH_4OAc$ pH 3.0
eluant B: 10 mM $NH_4OAc$ pH 3.0
flow rate: 0.8 ml/min
gradient:

| Time (min) | % Eluant A | % Eluant B |
|---|---|---|
| 0 | 5 | 95 |
| 20 | 40 | 60 |
| 60 | 60 | 40 |

Separation of Monosaccharides:

About 1 nmol in each case of derivatized glucose, fucose, xylose and fructose from the Merck Company are analysed as a monosaccharide mixture on an ODS Hypersil column. The linear gradient is 10–30% in 40 min with eluant A: 0.2% tetramethylethylenediamine in $H_2O/H_3PO_4$ pH 4.5 and eluant B: $CH_3CN$ at a flow rate of 1 ml/min [Anumuls K.R., (1994), Anal. Biochem. 220; 275]. The monosaccharides can be separated from one another.

Analysis of Acetylated Sugars:

About 1 nmol in each case of N-acetyl-neurarminosyl-2, 3-D-lactose and N-acetyl-neuraminic acid (Sigma), 0.5 nmol each of N,N'-diacetylchitobiose (Sigma) and N,N', N,N'',N'''-tetraacetylchitotetraose (Sigma) are derivatized with marker 4 and analysed together with 1 nmol derivatized glucose as a reference substance on an ODS Hypersil column. The gradient is 10–25% in 40 min with eluant A: 0.1% TFA in $H_2O$ and eluant B: 0.1% TFA in CH3CN at a flow rate of 1 ml/min. Also in this case it is possible to achieve a good separation of the mixture.

Analysis of Oligomaltose:

In the analysis of derivatized oligosaccharides about 1 nmol in each case of derivatized maltose, maltotetraose, maltopentaose and maltoheptaose from the Merck Company and 1 nmol derivatized glucose as a reference are applied to an ODS Hyypersil column. The gradient is 10–30% in 40 min with eluant A: 0.1% TFA in $H_2O$ and eluant B: 0.1% TFA om $CH_3CN$ at a flow rate of 1 ml/min. The saccharides are completely separated under these conditions.

Figure 4:
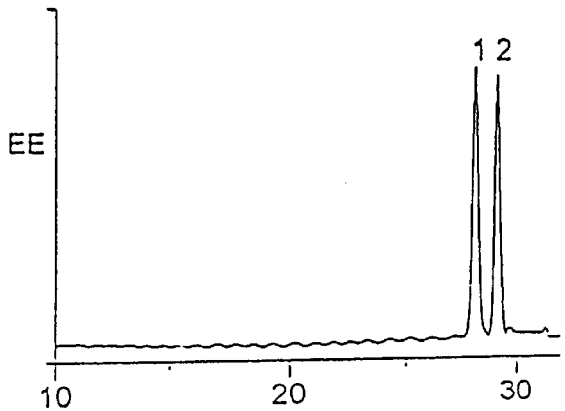
FIG. 4 shows the RP18 chromatogram of the reaction of 0.5 nmol in each case of the biantennary decasaccharide (2) and undecasaccharide (1) with HABA semicarbazide on an ODS Hypersil column (example 3)

Separation of Biantennary Oligosaccharides:

0.5 nmol in each case of derivatized biantennary sialylated decasaccharide and undecassaccharide (BioCarb) are analysed on an ODS Hypersil column. The gradient is 0–30% in 40 min with eluant A: 0.1% TFA in $H_2O$ and eluant B: 0.1% TFA in $CH_3CN$ at a flow rate of 1 ml/min. The saccharides that only differ by a sugar residue are completely separated (FIG. 4).

Analysis of Oligosaccharides of Glycoproteins:

In order to deglycosylate glycoproteins with the enzyme N-glycosidase F (Boehringer Mannheim) the glycoprotein (1 mg/ml) is denatured in 1% SDS solution by heating to 100° C. Subsequently 40 μl 0.5 M sodium phosphate pH 7.2, 10 μl water, 20 μl Nonidet P40® and 10 μl N-glycosidase F (200 U/ml) are added to 20 μl of the denatured glycoprotein. Complete deglycosylation is reached after 1 hour at 37° C. In a further mixture cleavage with Endo F2 (400 U/ml; Boehringer Mannheim) in 0.5 M sodium acetate pH 4.5 is carried out under otherwise identical conditions. Since the oligosaccharides accumulate as amine derivatives (Hauffe D., "GIT Fachz. Lab. 11 (1994), 1220–24) when cleaved with N-glycosidase F, these are converted into the OH form by acidifying to pH 4.5 (2 h at 25° C.).

Figure 5A:
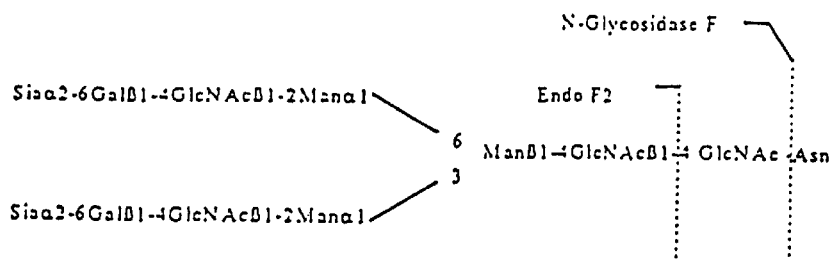
FIG. 5a shows the cleavage sites of the enzyme N-glycosidase F and endo F2 on the saccharide moiety of human transferrin (example 3a)
Figure 5B:
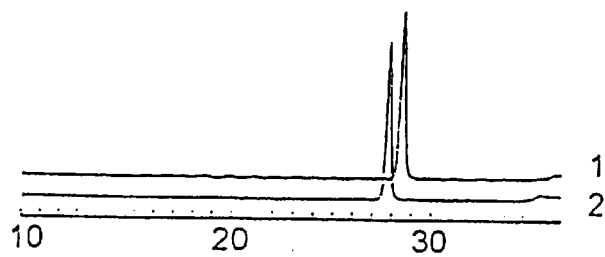
FIG. 5b shows the RP18 chromatogram of the saccharide moiety of human transferrin cleaved by endo F2 (1) or N-glycosidase F(2) after reaction with HABA-semicarbazide on an ODS Hypersil column (example 3a)

For the further reaction of the oligosaccharides with marker 4 the proteins are separated from the reaction mixture by ultrafiltration with a microconcentrator (Microcon 10) from the Amicon Company.

a) Human Transferrin:

The structure of the human transferrin oligosaccharide (Jamieson G. A., Jett M. & De Bernardo S. L., J. Biol. Chem. 246 (1971), 3686–3693) as well as the cleavage sites of Endo F2 and N-glycosidase F are shown in FIG. 5a. The oligosaccharides of 50 μg human transferrin (Boehringer Mannheim) cleaved off by endo F2 or N-glycosidase F each give one signal on RP-HPLC after derivatization (FIG. 5b). The retention times of the oligosaccharides cleaved off by the two enzymes on the ODS Hypersil column (gradient 0–30% in 40 min; eluant A: 0.1% TFA in $H_2O$, eluant B: 0.1% TFA in $CH_3CN$; flow rate 1 ml/min) correspond to the two standard saccharides biantennary decasaccharide and undecasaccharide (FIG. 4).

When the sialylated sugar derivative cleaved off by means of N-glycosidase F is applied to a mono Q HR 5/5 column with the volatile eluants triethylamine/acetic acid (eluant A: 10% $H_3CN$ adjusted to pH 9.3 with triethylamine and eluant B: 10% $H_3CN$ in 0.15 M triethylamine adjusted to pH 7.3 with acetic acid) a signal is obtained at about 20% eluant B.

b) Fetuin:

After cleaving the sugar residues of 60 μg Fetuin (Boehringer Mannheim) by means of N-glycosidase F analysis of the oligosaccharide derivatives on an anion exchange column (TSK DEAE-5PW Glas Pac; 75×8 mm from the LKB Company) under the elution conditions stated below yielded three signals which derive from di-, tri and tetrasialylated sugars (FIG. 6 lower part). The three sialylated main signals are also found by Green and Baenzinger [Green E. D. & Baenzinger J. U., Anal. Biochem. 158 (1986), 42–49] but in another distribution pattern.

When the fetuin sugar derivatives are digested by neuramidase (60 mU from C. perfringens; Boehringer Mannheim) for 2 h at 37° C. the oligosaccharide derivatives are no longer observed to bind to the anion exchange column after cleavage of the sialic acid derivatives. Only the asialo signal is observed (FIG. 6 top part).

eluant A: MeOH
eluant B: 0.1 M NaCl in MeOH
flow rate: 1 ml/min
gradient:

| Time (min) | % Eluant A | % Eluant B |
|---|---|---|
| 0 | 100 | 0 |
| 15 | 60 | 40 |
| 20 | 0 | 100 | c) Ribonuclease B:

Cleavage of high mannose type sugar residues of 20 μg ribonuclease B (Perkin Elmer) by N-glycosidase F yielded three resolved signals after derivatization of the sugar when analysed on an ODS Hypersil column (gradient 0–30% in 40 min; eluant A: 0.1% TFA in $H_2O$, eluant B: 0.1% TFA in $CH_3CN$; flow rate 1 ml/min). The distribution and intensity of the peaks corresponds to the known observations in the literature (Kakehi K., Suzuki S., Honda S. & Lee Y. C., Anal. Biochem. 199 (1991), 256–268). In the control with reaction mixtures of ribonuclease B without enzyme no signal is observed.

Deglycosylation of Biantennary Undecasaccharide with Exoglycosidases:

The sequential cleavage of sugar residues with exoglycosidases from a derivatized biantennary undecasaccharide with subsequent RP-HPLC analysis of the sugar residues on an ODS Hypersil column (gradient 10 30% in 40 min; eluant A: 0.1% TFA in HO, eluant B: 0.1% TFA in $CH_3CN$; flow rate 1 ml/min) results in a clear shift in the retention property of the sugars (FIG. 7). Cleavage of the sialic residues by neuraminidase leads as expected in this case to the greatest change in the retention properties. For the exoglycosidase digestion 1 nmol in each case of the derivatized sugar derivative in 100 μl 50 mM NaOAc buffer pH 5.5 is reacted for 1 h at 37° C. with the following enzyme combinations from Boehringer Mannheim. 50 mU neuramidase (*C.perfringens*), 8 U β-galactosidase (*E. coli*); 40 mU N-acetyl-β-D-glucosaminidase (*Diplococcus pneumoniae*) and 500 mU α-mannosidase (Jack bean).

EXAMPLE 4

Binding studies with Saccharide Conjugates on Streptavidin Microtitre Plates.

Saccharide conjugates can be bound onto microtitre plates coated with streptavidin (Boehringer Mannheim) with a capacity of ≧20 pmol biotin per well (=individual well of the microtitre plate). The sugar residues dissolved in 200 μl TBS (TBS=50 mM Tris/HCl, 150 mM NaCl pH 7.5) are immobilized while shaking gently (4 h at room temperature). In this process a maximum binding capacity of up to 20 pmol under saturating conditions (100 pmol sugar derivatives) is found for a large number of different saccharide derivatives (charged and uncharged monosaccharides and oligosaccharides).

In this method the bound sugar derivatives are detected on the one hand with various dixogigenin-labelled lectins (Boehringer Mannheim) and on the other hand via binding of an E-selectin fusion protein.

Binding studies with N-acetyl-neuraminosyl-2,3-D-lactose:

Derivatized N-acetyl-neuraminosyl-2,3-D-lactose in TBS is incubated for 4 h at room temperature on a microtitre plate coated with streptavidin as a model substance to test the standard conditions. After immobilization of the sugar derivative (0.5–20 pmol/well in the microtitre plate; dissolved in TBS) the wells are washed five times with 0.25 ml TBS. In order to bind the digoxigenin-labelled MAA lectin (specific for N-acetyl-neuraminosyl-α(2-3)Gal residues) 1–10 μg of the lectin is dissolved in 1 ml TBSM (TBSM= TBS containing 1 mM $MgCl_2$, 1 mM $MnCl_2$ and 1 mM $CaCl_2$) containing 0.5% blocking reagent (Boehringer Mannheim) and subsequently 0.2 ml of the lectin solution/well is incubated for 1 hour at room temperature while shaking gently. After the lectin has bound the wells are washed five times with 0.25 ml buffer (TBST=TBS containing 0.1% Tween-20®). Subsequently the wells are incubated with 0.2 ml of a solution of anti-digoxigenin-POD (0.3 U/ml; Boehringer Mannheim) in TBST for 1 h at RT while shaking gently. After the anti-digoxigenin-POD has bound the wells are washed five times with TBST. ABTS substrate solution for peroxidase is used for the detection (0.2 ml/well; Boehringer Mannheim). The colour development is read at 405 nm and RT after an incubation period of ca. 20 to 30 min. When 10 pmol of the sugar derivative is incubated on the plate the signal level increases linearly for the digoxigenin-labelled MAA lectin in the range 1–5 μg/ml. When increasing amounts of sugar derivatives (0.5–20 pmol) are used on the microtitre plate a linear increase in signal is found in the range 1–10 pmol saccharide, the detection limit for the N-acetyl-neuraminosyl-2,3-D-lactose derivative being at 0.5 pmol.

Binding Studies with Biantennary Undecasaccharide After Exoglycosidase Digestion:

After the sequential digestion of a biantennary undecasaccharide derivative (example 3) with the enzymes neuramidase (C. perfringens), β-galactosidase (*E. coli*); N-acetyl-β-D-glucosaminidase (Diplococcus pneumoniae) and α-mannosidase (Jack bean) it is possible to detect the individual digested saccharide derivatives on a streptavidin-coated microtitre plate. For this the respective oligosaccharide derivatives in TBS are immobilized for 4 h at RT on a microtitre plate. After washing the plate (5×0.25 ml TBS/well) the wells are incubated with 0.2 ml of a solution of the digoxigenin-labelled lectins SNA, DSA (concentration 5 μg/ml) and GNA (concentration 1 μg/ml) (1 h at RT). The detection is subsequently carried out analogously to the procedure described above.

In the digestion of the biantennary undecasaccharide shown in FIG. 8a significant absorbances are obtained in three cases when digoxigenin-labelled lectins are added (FIG. 8b):

In the case of SNA (specific for N-acety-lneuraminosyl-α(2-6)Gal residues) as the lectin in the reaction mixture containing the undigested undecasaccharide derivative.

In the case of DSA (specific for Gal(β1→4)GlcNAc residues) as the lectin in the reaction mixture containing the saccharide derivative digested by neuramidase.

In the case of GNA (specific for Man (β1→3)Man and Man (β1→6)Man residues) as the lectin in the reaction mixture containing the saccharide derivative digested with neuramidase, galactosidase and N-acetyl-β-D-glucosaminidase.

In contrast all other wells as well as the blank controls of the wells without sugar derivative or without lectin have absorbances below 5% which demonstrates the specificity of the lectins in this test.

A direct digestion of the biantennary undecasaccharide can also be carried out in the microtitre plate. For this 20 pmol of the derivative per well is immobilized for 4 h at RT and subsequently digested directly in the plate for 1 h at 37° C. with the enzymes described above. The sugar residues are detected analogously to the method described previously. The result is almost identical to the previous test.

Binding Studies with Oligosaccharides of Glycoproteins:

Oligosaccharides of fetuin cleaved by N-glycosidase F (example 3) have sialic acid residues at the non-reducing ends whose binding types α2-6 and α2-3 can be distinguished by means of the digoxigenin-labelled lectins SNA (specific for N-acetyl-neuraminosyl-α(2-6)Gal residues) and MAA (specific for N-acetyl-neuraminosyl-α(2-3)Gal residues).

Figure 9:
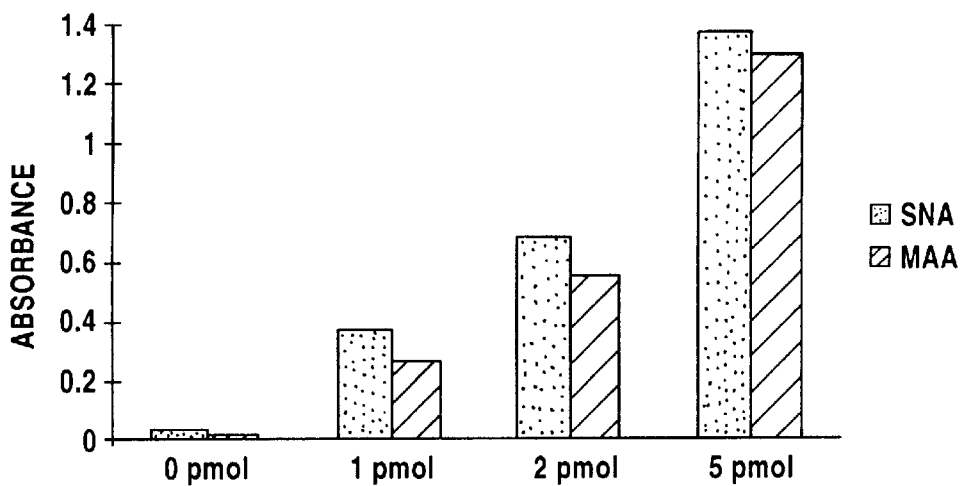
FIG. 9 shows the detection of increasing amounts of fetuin sugar derivatives using the digoxigenin-labelled lectins SNA and MAA (example 4)

For this 0–5 pmol in each case of the saccharide derivatives are immobilized in each well of a streptavidin-coated microtitre plate. 5 μg/ml digoxigenin-labelled lectin in TBSM is used in each case for the detection as described previously. FIG. 9 shows the result of this experiment with a fetuin sugar derivative as an example. Both lectins show distinct signals which increase linearly with increasing concentrations of the saccharide in the wells. The almost identical distribution that is found of α2-6 and α2-3-bound sialic residues corresponds to the values described in the literature (Green E. D., Adelt G., Baenzinger J. U., Wilson S. & Van Halbeek H., H. Biol. Chem., 263 (1988), 18253–68).

Figure 10:
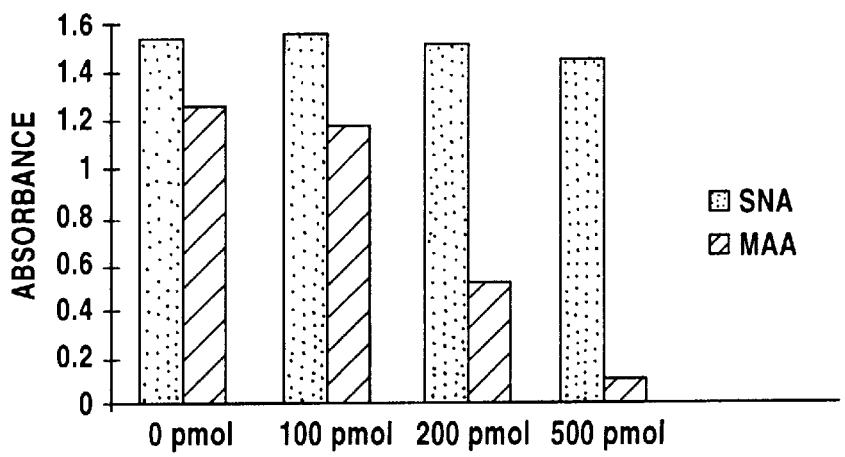
FIG. 10 shows the influence of increasing amounts of N-acetyl-neuraminosyl-2,3-D-lactose derivative on the detection of fetuin sugar derivatives using the digoxigenin-labelled lectins SNA and MAA (example 4)

When the digoxigenin-labelled MAA lectin is specifically inhibited by addition of N-acetyl-neuraminosyl-2,3-D-lactose in the lectin incubation of fetuin sugar derivatives (10 pmol) on the MTP a decrease of the signal strength can be observed at a 10-fold to 50-fold sugar excess in the wells (FIG. 10). The signal strength is about 50% of the value without inhibition when 200 pmol N-acetyl-neuraminosyl-2,3-D-lactose is added and about 15% when 500 pmol N-acetyl-neuraminosyl-2,3-D-lactose is added. As expected no inhibition occurs when the saccharide is added to the wells containing SNA as the lectin.

When the α2-3-bound N-acetyl-neuraminic acid of the fetuin sugar derivatives is specifically cleaved by means of NVD sialidase from Boehringer Mannheim (20 mU; 1 h at 37° C.) absorbance is no longer observed in the wells with MAA as the lectin.

In contrast the measurements with digoxigenin-labelled SNA as the lectin show almost the same absorbances as the untreated fetuin sugar derivatives (FIG. 11).

Analogous results are obtained in the detection of transferrin sugar derivatives with digoxigenin-labelled SNA lectin (concentration 5 μg/ml) and the ribonuclease B sugar derivatives with digoxigenin-labelled GNA lectin (concentration 1 μg/ml).

Binding Studies of E-selectin using 3'-sialyl Lewis X and 3'-sulfatyl Lewis X:

The two oligosaccharides 3'-sialyl Lewis X and 3'-sulfatyl Lewis X (1–5 pmol/well in each case; Oxford Glyco Systems) are bound as a conjugate to a streptavidin-coated microtitre plate. After binding of the sugar conjugate the wells are washed five times with 0.25 ml TBST and subsequently the wells are blocked with 1% BSA solution (1 h at RT). After removing the solution 0.5 μg of an E-selectin fusion protein is bound in the wells (soluble E-selectin fused to the κ-light chain expressed in SF-9 cells). After binding the receptor and washing the wells five times with TBST, anti-mouse Ig-POD (0.3 U/ml; Boehringer Mannheim) in TBST is bound. After washing with TBST the detection is carried out as described previously.

The signals for both derivatives increase linearly in the range 1–5 pmol of the saccharide derivatives (FIG. 12). Binding of E-selectin to the sugar derivatives in this case is strictly dependent on the addition of $Ca^{2+}$ ions (addition of 1 mM $CaCl_2$ to the buffer). The blank value controls of the wells without sugar derivative or without E-selectin or when $Ca^{2+}$ is complexed by EDTA (1 mM in the plate) yielded no measurable absorbances.

EXAPLE 5

Derivatization of N-acetyl-neuraminosyl-2,3-D-lactose with biotinyl-L-3-(2-naphthyl)-alanine hydrazide (BNAH)

a) Reactions:

For the reaction of N-acetyl-neuraminosyl-2,3-D-lactose for analytical purposes, 1 nmol of the saccharide is reacted for 6 h at 60° C. with a five-fold molar excess of biotinyl-L-3-(2-naphthyl)-alanine hydrazide (Boehringer Mannheim) in 100 μl MeOH/AcOH (9:1; v:v) in a closable Eppendorf cup. After the reaction only one signal of the reacted sugar derivative is observed on the HPLC (ODS Hypersil; eluant A: 0.1% TFA in $H_2O$; eluant B: 0.1% TFA in $CH_3CN$; gradient 0–50% in 30 min). On the TLC (mobile solvent: MeOH:$H_2O$:butane-3-one=6:2:2; v:v:v; detection of the sugars by means of 20% $H_2SO_4$ in EtOH) free sugar was no longer detectable after the derivatization from which a conversion rate of >95% can be concluded. The detection limit of the saccharide derivatives by means of fluorescence detection ($\lambda_{ex}$=275 nm and $\lambda_{em}$=324nm) is at ca. 10 pmol. The marker BNAH elutes from the RP18 column at ca. 35% $CH_3CN$ and can thus be readily separated from the conjugates which elute at 15–25% $CH_3CN$.

b) Stabilities:

The saccharide derivatives exhibit no manifestations of decomposition in solution at 25° C. (40 h) or after lyophilization which was confirmed by HPLC analysis. Separation of the dye excess:

Separation of the BNAH excess after reaction with the saccharides is achieved by extraction with ethyl acetate. For this 100 μl redistilled $H_2O$ and 800 μl ethyl acetate is added to 100 μl reaction mixtures; after mixing and centrifugation (1 min at 10000 g) the upper ethyl acetate phase is removed and the extraction is repeated a further two times with the lower aqueous phase. In this process 90% of the BNAH can be separated. The loss of sugar derivative tested with a glucose derivative is below the detection limit of 5%.

EXAMPLE 6

Binding Studies with N-acetyl-neuraminosyl-2.3-D-lactose on Streptavidin Microtitre Plates.

The derivatized saccharides dissolved in 200 μl TBS can be bound to streptavidin-coated microtitre plates while shaking gently (2 h at RT).

The maximum binding capacity is up to 20 pmol derivative/well under saturating conditions (100 pmol sugar derivative).

For the detection of N-acetyl-neuraminosyl-2,3-D-lactose the wells are washed five times with 0.25 ml TBS after immobilization of the sugar derivative (0.5–20 pmol/well in the microtitre plate; dissolved in TBS). For binding the digoxigenin-labelled MAA-lectin (specific for N-acetyl-neuraminosyl-α(2-3)Gal residues) 1–10 μg of the lectin is dissolved in 1 ml TBSM containing 0.5% blocking reagent and subsequently 0.2 ml of the lectin solution/well is incubated for 1 h at RT while shaking gently. After binding the lectin the wells are washed five times with 0.25 ml TBST buffer. Subsequently the wells are incubated for 1 h at RT with 0.2 ml of a solution of anti-digoxigenin-POD (0.3 U/ml) in TBST while shaking gently. After the binding of anti-digoxigenin-POD the wells are washed five times with TBST. The detection is achieved with 0.2 ml ABTS substrate solution/well for peroxidase (0.3 g/l). The colour development is read at 405 nm and RT after an incubation period of ca. 20 to 30 min. When increasing amounts of sugar derivatives are used (0.5–20 pmol) on the microtitre plate a linear increase in signal is found in the range 1–10 pmol, the detection limit for the N-acetyl-neuraminosyl-2,3-D-lactose derivative being 0.5 pmol.

What is claimed is:

1. Compound having a structure of the formula (I):

wherein

X is selected from the group consisting of —NR—$NH_2$, —C(A)—NR—$NH_2$ and —B—C(A)—NR—$NH_2$ in which R is hydrogen or an alkyl group with 1 to 4 carbon atoms and A and B each independently represent NH, O or S; and Y is a group

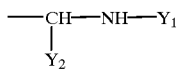

in which $Y_1$ denotes a naphthyl group and $Y_2$ is selected from the group consisting of —(($CH_2$)$_n V_q$)—K, —C(O)—($CH_2$)$_n$V)$_q$—K and —(($CH_2$)$_m$—W—($CH_2$)$_o$)$_p$—V-K in which V represents NH, O or S, K is biotin or a biotin compound that is capable of binding to streptavidin, avidin, or both, W represents NH or O, n=0 to 20, m=0 to 6, p=0 to 4 and q=0 or 1.

2. Compound as claimed in claim 1, wherein X—Y is biotinyl-L-3-(2-naphthyl)alanine hydrazide or the biotinyl group is replaced by a biotin compound that is capable of binding to streptavidin, avidin, or both.

3. Compound as claimed in claim 2, wherein the biotinyl group is replaced by a biotin compound that is capable of binding to streptavidin, avidin. or both.

4. Compound as claimed in claim 3, wherein the biotin compound that is capable of binding to streptavidin, avidin or both is selected from the group consisting of iminobiotin, diaminobiotin and desthiobiotin.

* * * * *